United States Patent [19]

Spatz

[11] Patent Number: 4,672,065

[45] Date of Patent: Jun. 9, 1987

[54] N-SUBSTITUTED PHENOXYACETAMIDE FUNGICIDES

[75] Inventor: David M. Spatz, Fairfax, Calif.

[73] Assignee: Chevron Research Company, San Francisco, Calif.

[21] Appl. No.: 730,874

[22] Filed: May 3, 1985

Related U.S. Application Data

[62] Division of Ser. No. 443,010, Nov. 19, 1982, Pat. No. 4,535,087.

[51] Int. Cl.$^4$ .................. A01N 43/48; C07D 237/20; C07D 239/42; C07D 241/20
[52] U.S. Cl. .................................... 514/255; 514/247; 514/256; 514/275; 544/224; 544/322; 544/327; 544/329; 544/332; 544/336
[58] Field of Search ............... 544/224, 322, 332, 336, 544/327, 329; 514/247, 255, 256, 275

[56] References Cited

U.S. PATENT DOCUMENTS

| 4,189,581 | 2/1980 | Scharwaechter et al. | 544/324 |
| 4,504,484 | 3/1985 | Sputz | 514/255 |
| 4,535,087 | 8/1985 | Sputz | 544/332 |

OTHER PUBLICATIONS

Henning et al., Paedagog, Hochsch, "Karl Liebknecht" Potsdam, 1977, 21(1) 47–59.
Henning et al., Chem. Abst. 90-103787z.
Schultz et al., Chem. Abst. 73-109499c.
Scharwaechter et al., Chem. Abst. 93-8210j.
Stubenrauch et al., Chem. Abst. 94-15736j.
Jikuhara et al., Chem. Abst. 97-162813x.

Primary Examiner—Mark L. Berch
Assistant Examiner—Cecilia Shen
Attorney, Agent, or Firm—S. R. LaPaglia; R. C. Gaffney; S. L. Biggs

[57] ABSTRACT

The N-substituted phenoxyacetamides of this invention are effective fungicides. In particular, these compounds are particularly effective against Tomato Late Blight.

24 Claims, No Drawings

N-SUBSTITUTED PHENOXYACETAMIDE FUNGICIDES

This is a continuation division of application Ser. No. 443,010, filed Nov. 19, 1982, now U.S. Pat. No. 4,535,087.

BACKGROUND OF THE INVENTION

This invention is drawn to novel fungicides.

With the world more dependent for food on an ever decreasing amount of cultivated farmland, it is increasingly important to develop effective fungicides which protect crops from fungicidal destruction.

Kozlik et al., in CA 79:53327Z, disclosed 1-carbamoylimidazoles as insecticidal.

Brookes et al., in U.S. Pat. Nos. 4,080,462 and 3,991,071, disclosed 1-(N,N-disubstituted carbamoyl and thiocarbamoyl)-imidazoles as fungicidal.

SUMMARY OF THE INVENTION

The compounds of the present invention are represented by the formula:

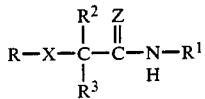

wherein R is phenyl, or phenyl substituted with 1 to 4 of the same or different substituents independently selected from fluoro, chloro, bromo, iodo, lower alkyl, trihalomethyl, or nitro;

$R^1$ is a 5- or 6-member heterocyclic ring containing 1 to 2 nitrogen atoms and the remainder of the ring atoms carbon atoms, optionally substituted with 1 to 2 independent lower alkyl groups with the proviso that a nitrogen of the 5- or 6-member heterocyclic ring is not bonded to the

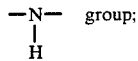

group;

$R^2$ and $R^3$ are independently hydrogen, or lower alkyl; X is sulfur, or oxygen; and
Z is sulfur, or oxygen.

Among other factors, the present invention is based on my finding that the compounds of this invention are effective fungicides. In particular, they possess good activity against Tomato Late Blight.

In part due to their superior fungicidal activity, preferred R groups include the trihalophenyl and dihalophenyl groups. Particularly preferred R groups are 2,4,6-trihalophenyl and 2,6-dihalophenyl.

Preferred halogens are chloro and bromo.

Preferred $R^1$ groups include, for instance, 3-pyridyl, 5-pyrimidyl, 3-pyrazyl, and 5-(1-methylimidazolyl).

Preferred $R^2$ and $R^3$ groups are hydrogen and methyl. Preferably, X and Z are oxygen.

DEFINITIONS

As used herein, the following terms have the following meanings, unless expressly stated to the contrary.

The term "alkyl" refers to both straight- and branched-chain alkyl groups. Generally, such alkyl groups contain from 1 through 12 carbon atoms.

The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "halo" or "halogen atom" refers to the groups fluoro, chloro, bromo and iodo.

The term "a 6-member heterocyclic ring containing 1 to 2 nitrogen atoms" refers to the groups pyridyl, pyridazinyl, pyrimidyl, pyrazinyl, and the like.

The term "a 5-member heterocyclic ring containing 1 to 2 nitrogen atoms" refers to the groups imidazolyl, pyrrolyl, pyrazolyl, and the like.

DETAILED DESCRIPTION OF THE INVENTION

The compounds of the present invention are prepared according to the following synthetic scheme:

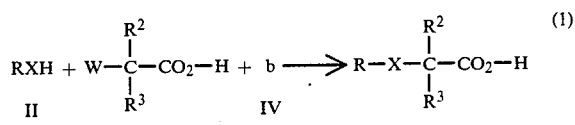

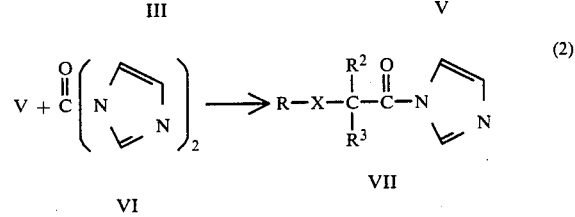

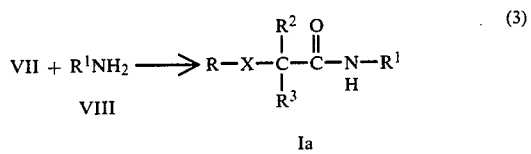

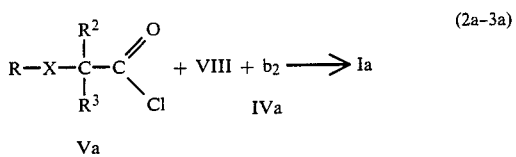

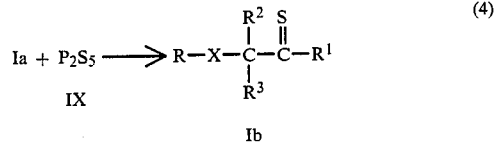

wherein R, $R^1$, $R^2$, $R^3$, X and Z are as defined above;
W is halogen;
b is a base; and
$b_2$ is an acid scavenger (base).

Reaction (1) is conducted by adding approximately 2 equivalents of base IV to II. The reaction is done in the liquid phase employing an organic solvent such as ethanol, methanol, and the like, or, alternatively, water. Preferably, the base employed is an inorganic base. Suitable inorganic bases include, for instance, sodium hydride, sodium methoxide, metallic sodium, and the like. After addition of IV, an approximately equimolar amount of III is added to the system. Reaction pressure is not critical and for convenience, the reaction is generally conducted at atmospheric pressure. The reaction is generally conducted at from 0° C. to 100° C., although preferably at from 40° C. to 70° C., and is generally complete from within 1 to 48 hours. The resulting intermediate, V, is isolated by conventional procedures such as extraction, filtration, chromatography, distillation, or alternatively, used in Reaction (2) without purification and/or isolation.

Reaction (2) is conducted by adding an essentially equimolar amount of carbonyldiimidazole, VI, to V. The reaction is conducted in the liquid phase using an inert anhydrous organic solvent such as chloroform, methylene chloride, dimethoxyethane, toluene, and the like. Reaction pressure is not critical and for convenience, the reaction is generally conducted at atmospheric pressure. The reaction is generally conducted at from 0° C. to 100° C., although preferably at room temperature, and is generally complete from within 1 to 24 hours. The resulting carboxylic acid imidazolide, VII, may be isolated by conventional procedures such as extraction, filtration, chromatography, distillation, and the like. Alternatively and preferably, the resulting intermediate is not isolated from the reaction solution but is used directly in Reaction (3).

Reaction (3) is conducted by adding an essentially equimolar amount of the appropriate primary amine, VIII, to VII. The reaction is conducted in the liquid phase using an inert anhydrous organic solvent such as chloroform, methylene chloride, dimethoxyethane, toluene, and the like. Preferably, the reaction solution is the same as was employed in Reaction (2) with the appropriate amine, VIII, merely added to the system after completion of Reaction (2). Reaction pressure is not critical and for convenience, the reaction is generally conducted at atmospheric pressure. The reaction is generally conducted at from 0° C. to 100° C., although preferably at room temperature, and is generally complete from within 1 to 24 hours. The product, Ia, is isolated by conventional procedures such as extraction, filtration, chromatography, distillation, or alternatively, used in Reaction (4) to prepare the compounds of formula I where Z is sulfur without purification and/or isolation.

Alternatively, Ia may be prepared according to Reaction (2a-3a) by adding a solution of the acid chloride corresponding to V to a solution of VIII. The acid chloride Va is prepared from the acid V by techniques known to the art, such as treatment with thionyl chloride. The reaction is conducted in the presence of $b_2$ (IVa), an acid scavenger such as triethylamine, pyridine, an alkylamine, sodium carbonate, or the like. The reaction is conducted in the liquid phase using an inert organic solvent such as methylene chloride, chloroform, dioxane, toluene, and the like. The reaction is carried out at a temperature of about −50° C. to about 100° C., preferably from about 0° C. to about 25° C. After the addition is complete, the reaction mixture is allowed to return to room temperature. The reaction is generally complete within about 0 to about 48 hours after the addition is complete. The resulting product Ia is isolated by conventional procedures such as extraction, filtration, chromatography, distillation, or alternatively used in Reaction (4) without further purification or isolation.

Reaction (4) is conducted by adding an essentially equimolar amount of phosphorus pentasulfide, IX, to Ia. The reaction is conducted in the liquid phase using an inert anhydrous organic solvent such as toluene, tetrahydrofuran, and the like. Preferably, the system is exposed to microwave radiation in order to facilitate the dispersion of phosphorus pentasulfide into solution. Reaction pressure is not critical and for convenience, the reaction is generally conducted at atmospheric pressure. The reaction is generally conducted at from 15° C. to 100° C., although preferably it is conducted at the ambient temperature and is generally complete from within 1 to 48 hours. The product, Ib, is then isolated by conventional procedures such as extraction, filtration, chromatography, distillation, and the like.

UTILITY

The compounds of the invention are effective in controlling fungal infections. In particular, some of the compounds of this invention are effective in controlling downy mildew fungal infections caused by the organism *Plasmopara viticola*. Some of the compounds of this invention are also useful for controlling leaf blights caused by organisms such as *Phytophthora infestans conidia, Alternaria solani conidia*, and *Septoria apii*. However, some fungicidal compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperatures and temperature ranges refer to the Centigrade system and the term "ambient" or "room temperature" refers to about 20° C. to 25° C. The term "percent" refers to weight percent and the term "mole" or "moles" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

EXAMPLE 1

Preparation of 2,4,6-trichlorophenoxyacetic acid 2,4,6-trichlorophenol, 100.7 gm, was added to 250 ml of ethanol. 228.6 ml of a 25% solution of sodium methoxide (2 equivalents) in methanol was then added to the system. The system was stirred at room temperature for approximately 1 hour. Afterwards, 69.5 gm of bromoacetic acid was added and the system was then heated to reflux. After 18 hours, an additional equivalent of sodium methoxide in methanol (114.3 ml) was added as well as 34.7 gm of bromoacetic acid. The system was continued at reflux for 12 hours. The reaction was then stopped and the solvent removed by stripping. The resulting solid was washed with water and then with ether. Concentrated HCl was next added to the solid precipitate and the system was left standing for 12 hours. Afterwards, the product was filtered, washed with water and air dried. Toluene was then added to the product. The toluene was removed by stripping and any remaining water was azeotroped off with the toluene. 74.4 gm of 2,4,6-trichlorophenoxyacetic acid was recovered.

EXAMPLE 2

Preparation of 2,6-dichlorothiophenoxyacetic acid 2,6-dichlorothiophenol, 50.0 gm, was added to 250 ml of ethanol. 63.8 ml of a 25% solution of sodium methoxide (2 equivalents) in methanol was then added to the system. The system was stirred at room temperature for approximately 3 hours. Afterwards, 20 ml of bromoacetic acid was added and the system was then heated to reflux. The system was continued at reflux for 16 hours. The reaction was then stopped and the solvent removed by stripping. The resulting material was dissolved with a basic aqueous solution and then washed with methylene chloride. Concentrated HCl was next added to the aqueous solution to acidify it. The product was extracted with methylene chloride. The methylene chloride solution was stripped and then triturated with hexane. The product was then filtered, washed with water and air dried to yield 5.3 gm of the 2,6-dichlorothiophenoxyacetic acid.

EXAMPLE 3

Preparation of 4-t-butylphenoxyacetic acid

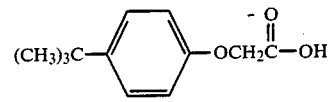

4-t-butylphenol, 37.5 gm, was added to 300 ml of ethanol. 57.2 gm of a 25% solution of sodium methoxide (2 equivalents) in methanol was then added to the system. The system was stirred at room temperature for approximately 0.5 hour. Afterwards, 29.5 ml of bromoacetic acid was added and the system then heated to reflux for 18 hours. The reaction was then stopped and the solvent removed by stripping. The resulting solid was dissolved in methylene chloride; dilute sodium hydroxide was added to give a basic pH. The resulting precipitate was dissolved in hydrochloric acid, and then extracted with methylene chloride. The methylene chloride was stripped and the resulting crude product air dried. Toluene was then added to the product. The toluene was removed by stripping and any remaining water was azeotroped off with the toluene to give 33.3 gm of 4-t-butylphenoxyacetic acid.

Similarly, by following the same procedures as followed in Examples 1 to 3 and using the appropriate starting material and reagents, the following are prepared:

2,4-dichlorophenoxyacetic acid;
2,4-dichlorothiophenoxyacetic acid;
α-methyl-2,4,6-trichlorophenoxyacetic acid;
α,α-dimethyl-2,4,6-trichlorophenoxyacetic acid;
2,4,6-tribromophenoxyacetic acid;

2,4,6-tribromothiophenoxyacetic acid;
2,4,6-trimethylphenoxyacetic acid;
2,4,6-trimethylthiophenoxyacetic acid;
4-nitrophenoxyacetic acid;
4-nitrothiophenoxyacetic acid;
3,5-di-(trifluoromethyl)phenoxyacetic acid; and
3,5-di-(trifluoromethyl)thiophenoxyacetic acid.

EXAMPLE 4

Preparation of
N-3-pyridyl-2,4,6-trichlorophenoxyacetamide (a) 2,4,6-trichlorophenoxyacetic acid, 23 gm, was added to 200 ml of methylene chloride along with 14.6 gm of carbonyl diimidazole. The system was stirred at room temperature for 16 hours to give the 2,4,6-trichlorophenoxyacetic acid imidazolide.

(b) 15.5 gm of 3-aminopyridine was then added to the system. The system was stirred at room temperature for 72 hours. The reaction was stopped and the methylene chloride solution was washed with water and then with saturated sodium bicarbonate solution. The methylene chloride solution was dried over magnesium sulfate and the methylene chloride removed by stripping. The product was purified by chromatography to yield 8.7 gm of the N-3-pyridyl-2,4,6-trichlorophenoxyacetamide, a white solid with a melting point of 113°–116° C. Listed as Compound No. 1 in Table I.

EXAMPLE 5

Preparation of
N-2-pyrazinyl-2,4,6-trichlorophenoxyacetamide

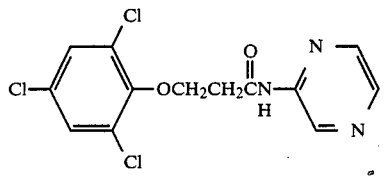

(a) To 200 ml methylene chloride, 23 gm of 2,4,6-trichlorophenoxyacetic acid and 14.6 gm of carbonyl diimidazole are added. The resulting mixture is stirred at room temperature for 16 hours to give the 2,4,6-trichlorophenoxyacetic acid imidazolide.

(b) To the system of Step (a), 15.6 gm of 2-aminopyrazine is then added. The system is stirred at room temperature for 72 hours. The reaction is stopped. The methylene chloride solution is washed first with water and then with a satured sodium bicarbonate solution. The methylene chloride solution is dried over magnesium sulfate. The methylene chloride is then removed by stripping and the resulting crude product is purified by chromatography to give the product.

Similarly, by following the procedures of Examples 4 and 5 and using the appropriate starting material and reagents, the following are prepared:
N-3-pyridyl-2,4,6-tribromophenoxyacetamide;
N-3-pyridyl-2,4,6-tribromothiophenoxyacetamide;
N-2-pyrimidyl-2,6-dichlorophenoxyacetamide;
N-2-pyrimidyl-2,6-dichlorothiophenoxyacetamide;
N-pyrazinyl-2,6-dichlorothiophenoxyacetamide;
N-pyrazinyl-2,6-dichlorophenoxyacetamide;
N-3-(1-methylpyrrolyl)-4-t-butylphenoxyacetamide;
N-3-(1-methylpyrrolyl)-4-t-butylthiophenoxyacetamide;
N-5-(1-methylimidazolyl)-2,4,6-trimethylphenoxyacetamide; and
N-5-(1-methylimidazolyl)-2,4,6-trimethylthiophenoxyacetamide.

EXAMPLE 6

Preparation of
N-3-pyridyl-2,4,6-trichlorophenoxythioacetamide

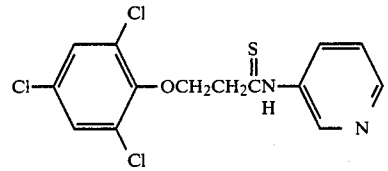

N-3-pyridyl-2,4,6-trichlorophenoxyacetamide, 33.4 gm, is added to 200 ml of toluene. 22.2 gm of phosphorus pentasulfide ($P_2S_5$) is then added to the system. The system is exposed to microwave radiation throughout in order to aid in the dispersion of the phosphorus pentasulfide. The reaction is stirred for 16 hours at ambient temperature. The reaction is then stopped and the solution filtered. The toluene is removed by stripping to give the title compound.

Similarly, by following the procedures of Example 6 and using the appropriate starting materials and reagents, the following are prepared:
N-3-pyridyl-2,4,6-tribromophenoxythioacetamide;
N-3-pyridyl-2,4,6-tribromothiophenoxythioacetamide;
N-2-pyrimidyl-2,6-dichlorophenoxythioacetamide;
N-2-pyrimidyl-2,6-dichlorothiophenoxythioacetamide;
N-pyrazinyl-2,6-dichlorophenoxythioacetamide;
N-pyrazinyl-2,6-dichlorothiophenoxythioacetamide;
N-3-(1-methylpyrrolyl)-4-t-butylphenoxythioacetamide;
N-3-(1-methylpyrrolyl)-4-t-butylthiophenoxythioacetamide;
N-5-(1-methylimidazolyl)-2,4,6-trimethylphenoxythioacetamide; and
N-5-(1-methylimidazolyl)-2,4,6-trimethylthiophenoxythioacetamide.

EXAMPLE A

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results are tabulated in Table II.

EXAMPLE B

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE C

Celery Late Blight

The Celery Late Blight tests were conducted using delery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table II.

EXAMPLE D

Tomato Early Blight

Compounds of the invention were tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The compounds tested and the results are tabulated in Table II.

EXAMPLE E

Grape Downy Mildew

The compounds of the invention were tested for the control of the Grape Downy Mildew organism *Plasmopara viticola*. Detached leaves, between 70 mm and 85 mm in diameter, 7-week-old *Vitis vinifera* cultivar Emperor grape seedlings were used as hosts. The leaves were sprayed with a 250-ppm solution of the test compound in acetone. The sprayed leaves were dried, inoculated with a spore suspension of the organism, placed in a humid environmental chamber and incubated at 66° F. to 68° F. and about 100% relative humidity. After incubation for 2 days, the plants were then held in a greenhouse 7 to 9 days; then the amount of disease control was determined. The percent disease control provided by a given test compound was based on the percent disease reduction relative to untreated check plants. The results are tabulated in Table II.

EXAMPLE F

Leaf Rust

The Leaf Rust test was made using pinto beans. The pathogen was *Uromyces phaseoli tipica*. The pinto bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° F. to 70° F. The plants were then removed from the chamber, allowed to dry, and then maintained in a greenhouse at a 60% to 80% relative humidity. The rate of infection on the leaves was made after about 14 days. The percent disease control provided by a given test compound was based on the percent disease reduction relative to untreated check plants. The results are reported in Table II.

EXAMPLE G

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 \times \left( \frac{\% \text{ disease in treated plants}}{\% \text{ disease in check}} \right)$$

The results are tabulated in Table II.

TABLE I

| No. | Compound | Carbon Calc. | Carbon Found | Hydrogen Calc. | Hydrogen Found | Nitrogen Calc. | Nitrogen Found | Form | m.p. |
|-----|----------|------|-------|------|-------|------|-------|------|------|
| 1 | 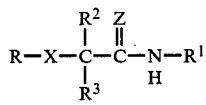 | 47.08 | 47.96 | 2.73 | 3.04 | 8.45 | 8.86 | white solid | 113–116° C. |

TABLE II

| | Fungicidal Activity % Control | | | | | | |
|---|---|---|---|---|---|---|---|
| Compound No. | GDM | TLB | CLB | TEB | BR | BPM | RB |
| 1 | 70 | 100 | 36 | 67 | — | — | 6 |

GDM — Grape Downy Mildew (*Plasmopara viticola*)
TLB — Tomato Late Blight (*Phytophthora infestans conidia*)
CLB — Celery Late Blight (*Septoria apii*)
TEB — Tomato Early Blight (*Alternaria solani conidia*)
BR — Bean Rust Eradicant (*Uromyces phaseoli tipica*)
BPM — Bean Powdery Mildew (*Erysiphe polygoni*)
RB — Rice Blast (*Piricularia oryzae*)

What is claimed is:

1. A compound of the formula:

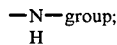

wherein R is 2,4,6-trihalophenyl or 2,6-dihalophenyl; $R^1$ is a 6-membered aromatic heterocyclic ring having two ring nitrogen atoms and the remainder carbon atoms or a 6-membered aromatic heterocyclic ring having two ring nitrogen atoms and the remainder carbon atoms with the ring substituted with 1 to 2 independent lower alkyl groups, with the proviso that a nitrogen of the 6-membered heterocyclic ring is not bonded to the —N—group;
 |
 H $R^2$ and $R^3$ are independently hydrogen or lower alkyl; X is sulfur or oxygen; and Z is sulfur or oxygen.

2. A compound of the formula defined in claim 1 wherein R is 2,4,6-trihalophenyl.

3. A compound of the formula defined in claim 2 wherein R is 2,4,6-trichlorophenyl.

4. A compound of the formula defined in claim 1 wherein $R^1$ is pyrazinyl or 2-pyrimidyl.

5. A compound of the formula defined in claim 1 wherein X and Z are oxygen.

6. A compound of the formula defined in claim 5 wherein $R^2$ and $R^3$ are hydrogen.

7. A compound of the formula defined in claim 6 wherein R is 2,4,6-trichlorophenyl.

8. A compound of the formula defined in claim 1 wherein $R^1$ is pyrazinyl or 5-pyrimidyl.

9. A compound of the formula defined in claim 7 wherein $R^1$ is pyrazinyl.

10. A compound of the formula defined in claim 7 wherein $R^1$ is 5-pyrimidyl.

11. A method for controlling fungi which comprises contacting said fungi or their growth environment with a fungicidally effective amount of the formula:

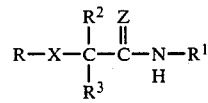

wherein R is phenyl, or phenyl substituted with 1 to 4 of the same or different substitutents independently selected from fluoro, chloro, bromo, iodo, lower alkyl, trihalomethyl, or nitro; $R^1$ is a 6-membered aromatic heterocyclic ring having two ring nitrogen atoms and the remainder carbon atoms or a 6-membered aromatic heterocyclic ring having two ring nitrogen atoms and the remainder carbon atoms with the ring substituted with 1 to 2 independent lower alkyl groups, with the proviso that a nitrogen of the 6-membered heterocyclic ring is not bonded to the —N—group;
 |
 H $R^2$ and $R^3$ are independently hydrogen or lower alkyl; X is sulfur or oxygen; and Z is sulfur or oxygen.

12. A method for controlling fungi which comprises contacting said fungi or their growth environment with a fungicidally effective amount of a compound of the formula defined in claim 2.

13. A method for controlling fungi which comprises contacting said fungi or their growth environment with a fungicidally effective amount of a compound of the formula defined in claim 4.

14. A method for controlling fungi which comprises contacting said fungi or their growth environment with a fungicidally effective amount of a compound of the formula defined in claim 9.

15. A method for controlling fungi which comprises contacting said fungi or their growth environment with a fungicidally effective amount of a compound of the formula defined in claim 10.

16. A method for controlling fungi which comprises contacting said fungi or their growth environment with a fungicidally effective amount of a compound of the formula defined in claim 7.

17. A fungicidal composition comprising a biologically inert carrier and a fungicidally effective amount of a compound of the formula defined in claim 1.

18. A fungicidal composition comprising a biologically inert carrier and a fungicidally effective amount of a compound of the formula defined in claim 2.

19. A fungicidal composition comprising a biologically inert carrier and a fungicidally effective amount of a compound of the formula defined in claim 4.

20. A fungicidal composition comprising a biologically inert carrier and a fungicidally effective amount of a compound of the formula defined in claim 9.

21. A fungicidal composition comprising a biologically inert carrier and a fungicidally effective amount of a compound of the formula defined in claim 10.

22. A fungicidal composition comprising a biologically inert carrier and a fungicidally effective amount of a compound of the formula defined in claim 7.

23. A method for controlling fungi which comprises contacting said fungi or their growth environment with a fungicidally effective amount of a compound of the formula defined in claim 8.

24. A fungicidal composition comprising a biologically inert carrier and a fungicidally effective amount of a compound of the formula defined in claim 8.

* * * * *